US00PP27229P3

(12) United States Plant Patent
Suphachadiwong

(10) Patent No.: US PP27,229 P3
(45) Date of Patent: Oct. 4, 2016

(54) ***VANDA* ORCHID PLANT 'SPCDW1312'**

(50) Latin Name: ***Vanda* hybrid**
Varietal Denomination: SPCDW1312

(71) Applicant: Thumrong Suphachadiwong, Chonburi (TH)

(72) Inventor: Thumrong Suphachadiwong, Chonburi (TH)

(73) Assignee: Suphachatwong Innovations (TH)

( * ) Notice: Subject to any disclaimer, the term of this patent is extended or adjusted under 35 U.S.C. 154(b) by 134 days.

(21) Appl. No.: 14/120,926

(22) Filed: Jul. 9, 2014

(65) Prior Publication Data

US 2015/0020264 P1 Jan. 15, 2015

(30) Foreign Application Priority Data

Jul. 10, 2013 (QZ) ..... PBR 2013/1922

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Cassandra Bright

(57) ABSTRACT

A new and distinct *Vanda* cultivar named 'SPCDW1312' is disclosed, characterized by unique flower color and large flower size. The new variety is a *Vanda*, typically produced as an indoor ornamental plant.

1 Drawing Sheet

Latin name of the genus and species: *Vanda* hybrid.
Variety denomination: 'SPCDW1312'.

BACKGROUND OF THE INVENTION

This application relates to a new cultivar of *Vanda* hybrid. The new variety is the product of a planned breeding program. The new variety originated as a seedling from the crossing of the unpatented, proprietary seed parent *Vanda* 'S243P' with the unpatented, proprietary pollen parent referred to as *Vanda* 'KMK96'. The crossing was made by the inventor in his research greenhouse in Chonburi, Thailand in December of 2001.

The new variety was first selected by the inventor, Thumrong Suphachadiwong, a citizen of Thailand, in November of 2006 in a research greenhouse belonging to the inventor in Chonburi, Thailand. After identifying the new variety as a potentially interesting selection, the inventor continued confidential testing and propagation of 'SPCDW1312', assessing stability of the unique characteristics of this variety.

Asexual reproduction of the new cultivar 'SPCDW1312' was first performed at a commercial laboratory belonging to the inventor in Chonburi, Thailand by tissue culture in June of 2007. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SPCDW1312' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1312'. These characteristics in combination distinguish 'SPCDW1312' as a new and distinct *Vanda* cultivar:

1. Unique magenta flower color.
2. Large flowers
3. Thick petals
4. Tesslation pattern of petals.

PARENT COMPARISON

Plants of the new cultivar 'SPCDW1312' are similar to the seed parent, *Vanda* 'S243P' in most horticultural characteristics. However the new variety, 'SPCDW1312' differs from 'S243P' in the following characteristics:

1. Stronger and better arranged flower spikes.
2. Flower is thicker.
3. Pink coloration is darker and flower has tessellation. Seed parent flower color is lighter pink and without tessellation.

Plants of the new cultivar 'SPCDW1312' are similar to the pollen parent, *Vanda* 'KMK96' in most horticultural characteristics. However the new variety, 'SPCDW1312' differs from 'KMK96' in the following characteristics:

1. Brighter pink flower color than the pollen parent.
2. Larger flower size.
3. Larger plant size.

COMMERCIAL COMPARISON

'SPCDW1312' is similar in most horticultural characteristics to the unpatented commercial variety *Vanda* 'SPCDDW1111' in most horticultural characteristics. However the new variety, 'SPCDW1312' differs from 'SPCDDW1111' in the following characteristics:

1. The new variety has a magenta hued flower color, compared to the purple flower of this comparator.
2. Different petal and sepal shape.
3. Weaker flower netting.
4. Petals are closer together.

'SPCDW1312' is similar in most horticultural characteristics to the unpatented commercial variety *Vanda* 'Hot Magenta' in most horticultural characteristics. However the new variety, 'SPCDW1312' differs from 'Hot Magenta' in the following characteristics:

1. Lighter flower color.
2. Flowers have wider dorsal sepals.
3. Larger lateral lobes.
4. Broader lips.

BRIEF DESCRIPTION OF THE PHOTOGRAPH

The accompanying photograph in FIG. 1 illustrates in full color a typical plant of 'SPCDW1312' grown in a commercial greenhouse in Honselersdijk, the Netherlands. The plant is 5½ to 6½ years old. Described plant not container-grown, but in a hanging basket without soil. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1312' plants grown in a commercial greenhouse in Honselersdijk, the Netherlands. The plant is 5½ to 6½ years old. Described plant is in a hanging basket without soil. Temperatures ranged between 19° C. and 23° C. day and night. No photoperiodic or chemical treatments were given to the plants. During bright Summer conditions. shade was given. During dark Winter months, no supplemental light was given. Measurements and numerical values represent averages of typical plant types.

Botanical classification: *Vanda* hybrid 'SPCDW1312'.

PROPAGATION

Type of propagation typically used: Tissue culture.

Time to produce a rooted cutting/liner: The time needed from for the start of a mericlone to get the small plants ready for deflasking is approx. 24 months under a controlled temperature of about 26 degrees Celsius. After that period they have matured roots. They start to make roots in the last 6 months in flasks. After deflasking they remain in shaded conditions under local outdoor temperatures Root description: Moderately to heavy rooting with aerial roots only. Roots very fleshy. non-fibrous. Average length of old roots: 32.0 cm, average diameter of old roots: 0.3 mm, average diameter of young roots: 0.5 cm. Old roots colored yellow-green; near RHS 146D. Young roots colored greyed-green; near RHS 192D, growing tips of roots yellow-green: 152A.

PLANT

Growth habit: Monopodial, upright.

Height to top of foliage: Average height from base (plant grown in hanging basket, so no soil line present) to top of foliage: 34.8 cm.

Height to top of flowers: Average height from base (plant grown in hanging basket, so no soil line present) to top of flowers: 51.8 cm.

Plant spread: Average: 47.7 cm.

Normal pot size: Hanging basket (8×8 cm square).

Growth rate: Moderate.

Number of leaves per plant: Average: 26.

FOLIAGE

Leaf:

*Arrangement*.—Distichous.

*Average length*.—Approximately 25.4 cm.

*Average width*.—Approximately 2.7 cm.

*Shape of blade*.—Ligulate, strongly carinate.

*Aspect*.—Slightly curved.

*Apex*.—Unequal praemorse.

*Base*.—Sheathing. Sheath length: Average 1.8 cm. Sheath width: Average 1.4 cm. Sheath color: Yellow-green; near RHS 146C and 146D.

*Margin*.—Entire.

*Texture of top surface*.—Glabrous, matte.

*Texture of bottom surface*.—Glabrous, matte.

*Color*.—Young foliage upper side: Green to yellow-green; in between near RHS 143A and 144A. Young foliage under side: Yellow-green; near RHS 144A. Mature foliage upper side: Yellow-green; near RHS 144A but slightly darker. Mature foliage under side: Yellow-green; in between near RHS 144A and 144B.

*Venation*.—Type: Parallel. Venation coloration: As leaf surface; upper side yellow-green; slightly darker than RHS 144A, under side yellow-green; in between near RHS 144A and 144B.

Petiole: No petioles present, leaves sessile.

FLOWERING CHARACTERISTICS

General description: Typical for *Vanda* in shape of inflorescence and individual flowers.

*Lastingness of bloom*.—Approximately 10 weeks.

Flower bud:

*Rate of opening*.—Buds open approx. three weeks from first sight.

*Length*.—Average: 1.5 cm.

*Diameter*.—Average: 1.4 cm.

*Shape*.—Broad obovate.

*Color*.—Purple; near RHS N77D, top tinged greyed-purple; near RHS 183D, base yellow-green; near RHS 145C.

Peduncle:

*Length*.—Approximately 35.0 cm.

*Width*.—Approximately 0.6 cm.

*Aspect*.—Approximately 30° angle to rosette.

*Strength*.—Strong.

*Texture*.—Smooth, moderately glossy.

*Color*.—Yellow-green; near RHS 144B.

Inflorescence:

*Flowers per stem*.—Average: 10.

*Inflorescence arrangement*.—Axially placed raceme.

*Inflorescence height*.—Approximately 24.8 cm (measured from base of lowest flower to top of upper flower).

*Inflorescence width*.—Approximately 18.0 cm.

Individual flowers:

*Flower type*.—Zygomorphic (orchidaceous), typical shape for the genus *Vanda*.

*Shape*.—Zygomorphic, consisting of three sepals and three petals, one of which is transformed into a labellum (lip).

*Length* (*height*).—Approximately 10.2 cm.

*Width*.—Approximately 10.1 cm.

*Depth*.—Approximately 3.5 cm.

*Fragrance*.—No fragrance.

*Persistent*.—No.

*Quantity of petals*.—3, consisting of 2 "traditional petals and a labellum (lip), described separately.

Petals:

*Arrangement*.—One lateral petal on each side.

*Length*.—Approximately 4.7 cm.

*Width*.—Approximately 4.6 cm.

*Shape*.—Near orbicular to reniform.

*Apex*.—Obtuse.

*Base*.—Cuneate.

*Margin*.—Entire.

*Texture*.—Upper forward surface: Glabrous, matte, velvety.

*Texture*.—Lower back surface: Glabrous, matte, velvety.

*Color*.—When opening, forward surface: Purple; near RHS N78B, colored violet towards the top and margins; near RHS N80B and N80C. When opening, back surface: Purple-violet; near RHS N81B and N81C. Fully Opened, forward surface: Purple-violet; near RHS N80B, with a dense reticulate veining colored purple; near RHS N78A but very slightly more red-purple. Fully Opened, back surface: Purple-violet; near RHS N80B, with a dense reticulate veining colored purple; near RHS N78A to N78B. Fading, forward surface: Not fading. Fading, back surface: Not fading. Color Venation Fully Opened. forward surface: Main veins purple; near RHS N78A. Color Venation Fully Opened, back surface: Main veins purple; near RHS N78A to N78B.

Labellum/lip:

*Shape*.—Three-lobed, lateral lobes involute, central lobe slightly revolute.

*Length*.—Approximately 2.1 cm

*Width*.—Approximately 1.4 cm.

*Texture*.—Glabrous, slightly glossy, with 3 callosities.

*Tip*.—Emarginate.

*Base*.—Cuneate.

*Color*.—When opening, forward surface: Lateral lobes purple; near RHS N78B to N78C, base lighter; 77D, with an orange basal spot; near RHS 26A. Central lobe and callosities purple; near RHS N78A, base lighter; near RHS N78B, tip more red-purple; near in between 71A and N78A but slightly darker. When opening, back surface: Lateral lobes purple; near RHS N78D. striped darker towards the base; near RHS N78C. Central lobe red-purple; near RHS 72A, base lighter; near RHS 72B. Fully Opened, forward surface: Lateral lobes purple; near RHS N78B to N78C, base lighter; 75B and 75C, with an orange basal spot; near RHS 26A. Central lobe and callosities purple; near RHS N78A, base lighter; near RHS N78B, tip more red-purple; near in between 71A and N78A but slightly darker. Fully Opened, back surface: Lateral lobes purple; near RHS N78D, striped darker towards the base; near RHS N78C. Central lobe red-purple; near RHS 72A, base lighter; near RHS 72B. Fading, forward surface: Not fading. Fading, back surface: Not fading. Color Venation Fully Opened, forward surface: No venation visible on labellum. Color Venation Fully Opened, back surface: No venation visible on labellum.

*Margin*.—Entire.

Spurs:

*Quantity*.—Average: 1.

*Appearance*.—Short triangular, in line with central lobe of labellum.

*Length*.—Approximately 0.9 cm.

*Width*.—Approximately 0.4 cm.

*Height*.—Approximately 0.7 cm (at the base).

*Shape*.—Short triangular.

*Apex*.—Obtuse.

*Base*.—Broad cuneate.

*Margin*.—Entire.

*Texture*.—Glabrous, very slightly glossy.

*Color*.—Purple; near RHS 76C to 76D, striped darker; near RHS N78C and N78D.

Sepals:

*Quantity*.—Average: 3.

*Appearance*.—One dorsal sepal (pointing, upright) and two lateral sepals.

*Length*.—Dorsal sepal approximately 5.0 cm. Lateral sepals approximately 5.2 cm.

*Width*.—Dorsal sepal approximately 4.6 cm. Lateral sepals approximately 5.3 cm.

*Shape*.—Dorsal sepal broad ovate. Lateral sepals near orbicular.

*Apex*.—Obtuse.

*Base*.—Cuneate.

*Margin*.—Entire.

*Texture*.—Glabrous, matte, velvety.

*Color*.—Dorsal sepal purple-violet; near RHS N80B, with a dense reticulate veining colored purple; near RHS N78A. Lateral sepals purple-violet; near RHS N80B, with a dense reticulate veining colored purple; near RHS N78A and N78B.

Pedicels:

*Length*.—Approximately 5.4 cm.

*Diameter*.—Approximately 0.55 cm.

*Angle*.—Approximately 70° angle to peduncle.

*Strength*.—Very strong.

*Texture*.—Glabrous, axially angled with 5 "ribs", axially twisted (due to resupination), glossy.

*Color*.—Purple; near RHS 75C, tinged white near distal end; near RHS N155B.

REPRODUCTIVE ORGANS

*Stamens, style and stigma fused into column*?.—Yes.

*Column length*.—Approximately 0.6 cm.

*Column diameter*.—Approximately 0.7 cm.

*Column color*.—White; near RHS N155B, upper side tinged purple; N78D.

*Ovary*.—Position: Inferior. Diameter: Approximately 0.5 cm. Color: White; near RHS 155A.

*Pollinia color*.—Yellow-orange; near RHS 15A to 15B.

OTHER CHARACTERISTICS

Disease resistance: Neither resistance nor susceptibility to the normal diseases found in *Vanda* has been observed.

Drought tolerance and cold tolerance: Tropical Orchid, does not tolerate cold or drought.

Fruit/seed production: No fruits/seeds detected to date.

What is claimed is:

1. A new and distinct cultivar of *Vanda* plant named 'SPCDW1312' as herein illustrated and described.

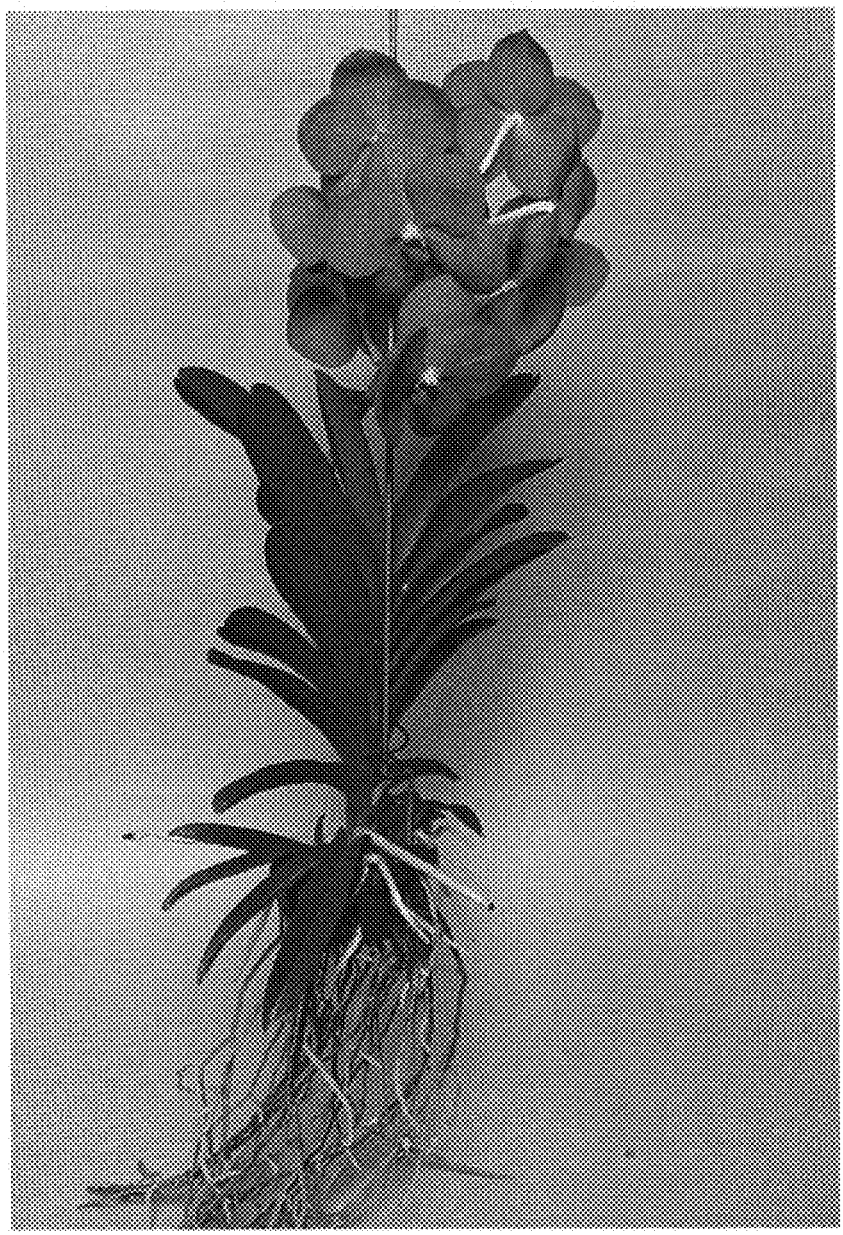

* * * * *